United States Patent [19]

Posner et al.

[11] Patent Number: 6,043,386
[45] Date of Patent: Mar. 28, 2000

[54] NON-CALCEMIC, ANTIPROLIFERATIVE, TRANSCRIPTIONALLY ACTIVE 24-FLUORINATED HYBRID ANALOGS OF 1α,-25-DIHYDROXY VITAMIN $D_3$

[75] Inventors: Gary H. Posner, Baltimore, Md.; Jae Kyoo Lee, San Diego, Calif.; Qiang Wang, Baltimore, Md.

[73] Assignee: John Hopkins University, Baltimore, Md.

[21] Appl. No.: 09/323,106

[22] Filed: Jun. 1, 1999

Related U.S. Application Data

[60] Provisional application No. 60/088,035, Jun. 3, 1998.
[51] Int. Cl.[7] .......................... C07C 401/00; A61K 31/59
[52] U.S. Cl. ........................ 552/653; 552/653; 514/167
[58] Field of Search ........................... 552/653; 514/167

[56] References Cited

U.S. PATENT DOCUMENTS

| | | | |
|---|---|---|---|
| 4,421,690 | 12/1983 | Partridge et al. | 260/397.1 |
| 4,599,330 | 7/1986 | Boris et al. | 514/167 |
| 4,853,378 | 8/1989 | Hamma et al. | 514/167 |
| 4,868,165 | 9/1989 | Ikekawa | 514/167 |
| 4,970,203 | 11/1990 | DeLuca et al. | 514/167 |
| 5,830,885 | 11/1998 | Posner | 514/167 |

OTHER PUBLICATIONS

Vanham et al. (J. Steroid Chem. Biochem. (1988), 29(4), 381–6), 1988.

*Primary Examiner*—Jose C. Dees
*Assistant Examiner*—Sabiha N. Qazi
*Attorney, Agent, or Firm*—Pillsbury Madison & Sutro LLP

[57] ABSTRACT

Fluorinated analogs of 1α,25-dihydroxyvitamin $D_3$. These analogs are synthesized in a convergent manner by joining A-ring and C,D-ring fragments. Each hybrid analog, having a calcemia-lowering 1-hydroxymethyl group and a potentiating 16-ene-24,24-difluorinated C,D-ring and side chain, is designed to be lipophilic and inert toward 24-hydroxylase enzyme catabolism. Each hybrid analog with 1β,3α-substituent stereochemistry shows a pharmacologically desirable combination of high antiproliferative and high transcriptional activities in vitro and also low calcemic activity in vivo.

6 Claims, 3 Drawing Sheets

NON-CALCEMIC, ANTIPROLIFERATIVE, TRANSCRIPTIONALLY ACTIVE 24-FLUORINATED HYBRID ANALOGS OF 1α,-25-DIHYDROXY VITAMIN D₃

This application claims priority to U.S. provisional application Ser. No. 60/088,035, filed Jun. 3, 1998, which is incorporated herein by reference.

Development of the invention was supported by grants from the National Institutes of Health. The U.S. government has certain rights in the invention.

FIELD OF THE INVENTION

The present invention relates to novel analogs of the hormone 1α,25-dihydroxy vitamin $D_3$. Such analog materials exhibit a pharmacologically desirable combination of high antiproliferative and high transcriptional activity in vitro along with no or low calcemic activity in vivo.

BACKGROUND OF THE INVENTION

Because of its extraordinarily high potency in regulating diverse biochemical events vital to good health in humans, 1α,25-dihydroxy vitamin $D_3$, also known as calcitriol or 1,25$D_3$, has stimulated the worldwide interest of medical researchers, molecular biologists, pharmacologists, medicinal and organic chemists, and researchers in the area of products for personal care and cancer prevention and/or treatment. Its structure is shown in Formula 1.

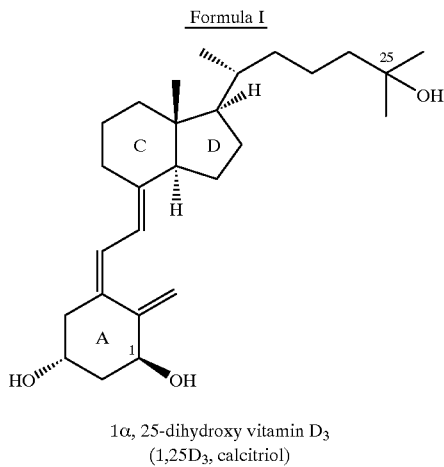

1α, 25-dihydroxy vitamin $D_3$
(1,25$D_3$, calcitriol)

A major chemical challenge has been to design and synthesize analogs of 1α,25-dihydroxy vitamin $D_3$ that retain potent antiproliferative and pro-differentiating activities but that lack hypercalcemic activity. Such analogs should be useful in such applications as skin care, cancer prevention and chemotherapy, and for treatment of neurodegenerative and immunological diseases.

Some synthetic analogs exhibiting such selective physiological activities, like 1α,25-dihydroxy-16-ene-23-yne-26,27-hexafluorocholecalciferol developed by Hoffman-La Roche, have been shown to possess very desirable pharmacological properties. Other useful analogs have been described in U.S. Pat. Nos. 5,403,832 and 5,830,885.

Only a few 24-fluoro and 24,24-difluoro analogs of 1,25$D_3$, having natural A-ring substituents and stereochemistry, have been synthesized. They have been shown, however, to be disappointingly similar to 1,25$D_3$ in terms of calcemic activity. Although their binding affinity to the vitamin D receptor (VDR) is similar to that of calcitriol, such materials do have longer plasma half-lives.

Given the foregoing, it is clear that there is a continuing need to identify additional synthetic analogs of the hormone 1α,25-dihydroxy vitamin $D_3$, which analogs selectively exhibit desirable pharmacological activities but do not exhibit hypercalcemic activity. Accordingly, it is an object of the present invention to provide novel 1,25$D_3$ analogs which are useful for a wide variety of beneficial medicinal and/or personal care product uses but which do not exhibit undesirably high levels of calcemic activity in vivo.

SUMMARY OF THE INVENTION

The present invention relates to novel fluorinated analogs of 1α,25-dihydroxy vitamin $D_3$. Such analogs have the general structural formula set forth in Formula II.

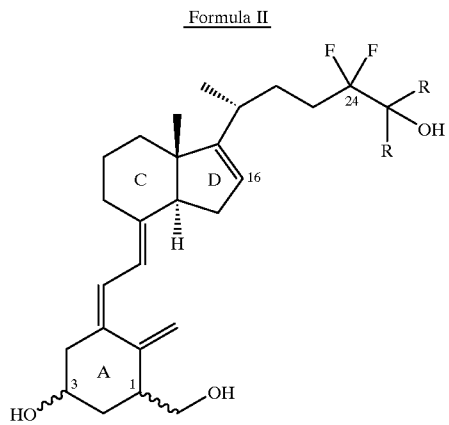

In Formula II, the hydroxymethyl substituent at Positions 1 and the hydroxy substituent at Position 3 on the A-ring can be such that the analogs are either in the (–), i.e., (1α, 3β), or the (+), i.e., (1β, 3α), diastereoisoneric configuration. The R group is a $C_1$–$C_4$ straight-chained or branched alkyl group or a $C_{1-7}$ cycloalkyl group. In preferred embodiments, R is a methyl or ethyl group.

BRIEF DESCRIPTION OF THE DRAWINGS

FIG. I is a graph showing dose response effects of the vitamin $D_3$ analogs herein on keratinocyte proliferation.

FIG. II is a graph showing dose response effects of the vitamin $D_3$ analogs herein on malignant melanoma cell proliferation.

Figure 1:
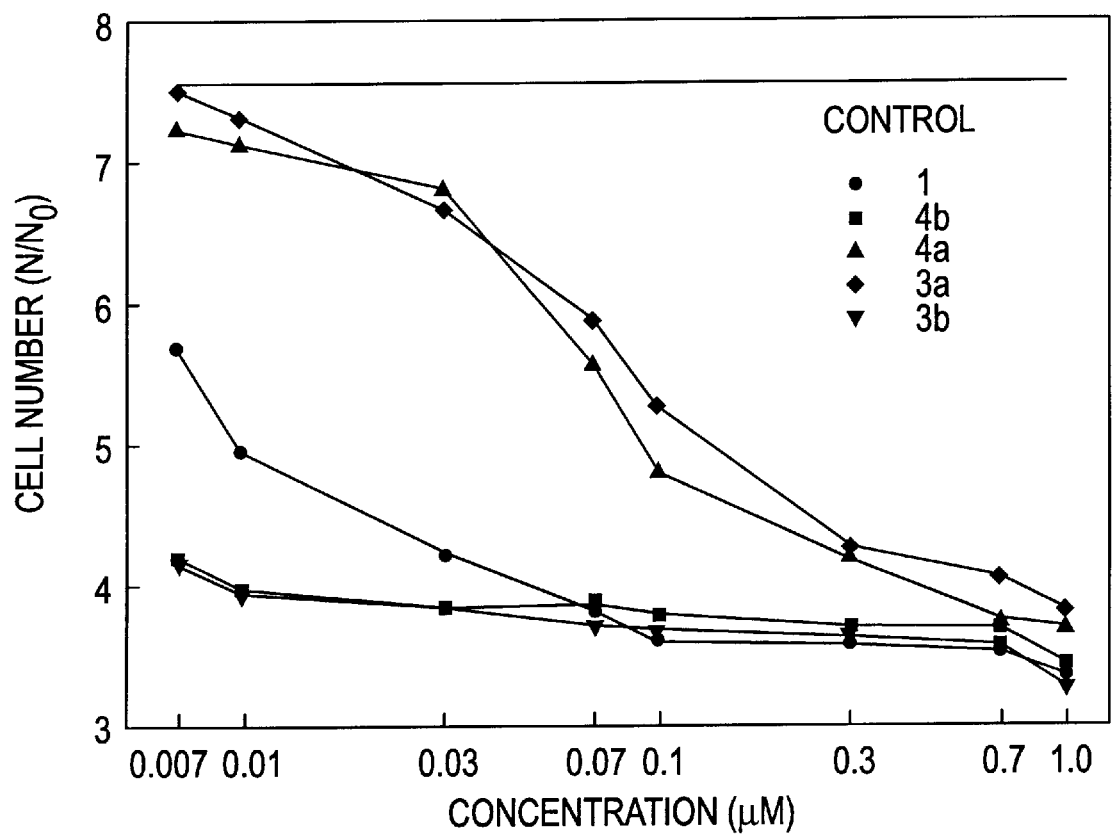

FIG. III is a graph showing the effects of the vitamin $D_3$ analogs herein on urinary calcium excretion in rats.

DETAILED DESCRIPTION OF THE INVENTION

In preparing the 16-ene-24-gem-difluoro vitamin $D_3$ analogs corresponding to Formula II, several considerations are taken into account in order to arrive at the desired combination of substituents which will diminish calcemic activity yet also provide potently pro-differentiating side chains. Position 24 on the side chain is typically the site of side chain metabolic oxygenation. Therefore, it is believed that replacing C—H by stronger C—F bonds at this position should increase lifetime of such an analog in vivo. Further, the atomic size of a fluorine substituent closely matches that of a hydrogen atom, thereby causing no steric hindrance to receptor binding. Further, it is postulated that the presence of two fluorine atoms should increase the lipophilicity of the hybrid analog relative to its non-fluorinated counterpart, thereby enhancing rates of absorption and transport in vivo. Finally, a 16-ene carbon-carbon double bond often potentiates antiproliferative activity.

Taking these considerations into account, the 16-ene-gem-difluoro analogs of the present invention can be prepared via a multi-step organic synthesis reaction procedure as set forth hereinafter in Scheme I.

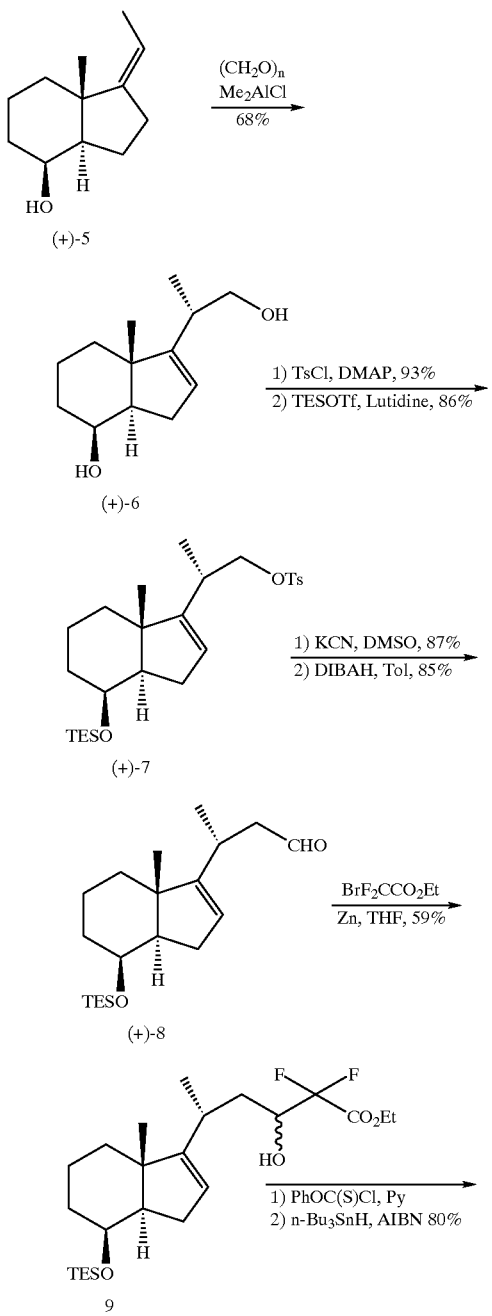

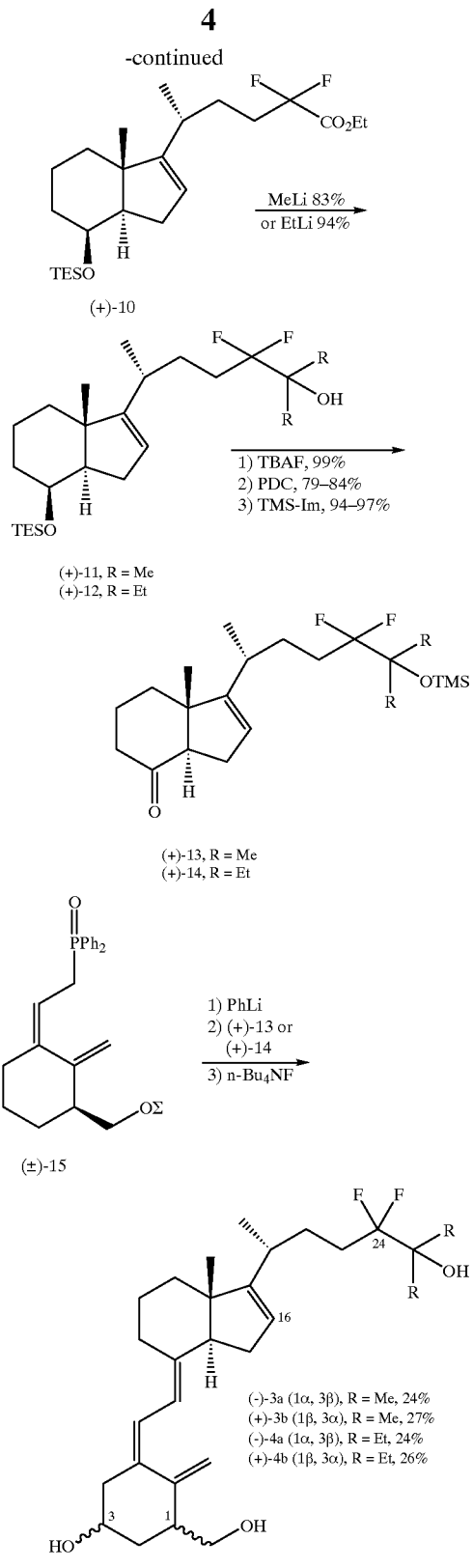

Referring to Scheme I, a known unprotected hydroxy olefin (+)-5 is reacted with dimethylaluminum chloride and paraformaldehyde via an ene process to give homoallylic diol (+)-6 stereoselectively. (See Posner et al.; *J. Org. Chem.*, 1997; 62; pp. 3299–3314.) After tosylation of the primary hydroxyl group and silylation of the secondary hydroxyl group, tosylate (+)-7 is converted into the corresponding nitrile that is reduced to form one-carbon homologated aldehyde (+)-8. A Reformatsky reaction using ethyl bromodifluoroacetate and activated zinc (See Haiilnan et al., *Tetrahedron Lett.*, 1984, 25, pp. 2301–23302.) gives gem-difluoro ester alcohol 9 as a 1:1 ratio of diastereomers. (See Kondo et al.; *Chem. Pharm. Bull.*, 1996; 44; pp. 62–66.) Barton radical deoxygenation at C-23 proceeds without loss of the adjacent 24-fluorine atoms to give difluoro ester (+)-10. Although Grignard addition of a methyl group to this ester proceeds in moderate yield, use of ethylmagnesium chloride causes mainly reduction of the ester functionality. In contrast, both methyllithium and ethyllithium cleanly convert this ester (+)-10 into the corresponding tertiary alcohols (+)-11 and (+)-12. Fluoride-induced desilylation, C-8 oxidation, and finally C-25 hydroxyl silylation gives enantiomerically pure C,D-ring ketones (+)-13 and (+)-14. Coupling of these C,D-ring chirons with racemic A-ring allylic phosphine oxide (±)-15 (See Dai et al., *Synthesis* 1994, pp.1383–1398.), followed by desilylation then produces the target hybrid analogs 3 and 4. Separation of diastereomers by HPLC. gives enantiomerically pure hybrid analogs (−)-3a, (+)-3b, (−)-4a, and (+)-4b.

Within each pair of diastereomers shown in Scheme I, tentative stereochemical assignment can be achieved based primarily on characteristic 400 MHz $^1$H NMR signals. Such results are set forth in Table I.

TABLE I

| analogs | C-18 | C-19a | C-19b | $[\alpha]25D$ |
|---------|------|-------|-------|---------------|
| 3a | 0.68 | 5.18 (d, 1.6 Hz) | 5.03 (d, 2.0 Hz) | −14° |
| 3b | 0.66 | 5.16 (dd, 2.0, 0.8 Hz) | 5.00 (d, 2.0 Hz) | +93° |
| 4a | 0.68 | 5.18 (d, 1.6 Hz) | 5.03 (d, 2.0 Hz) | −1.3° |
| 4b | 0.66 | 5.15 (d, 0.8 Hz) | 5.00 (d, 1.6 Hz) | +78° |

Preparation of the different hybrid analogs, Structures 3a, 3b, 4a, and 4b of Scheme I, is illustrated by the following Examples I–IX. The biological activity of these analogs is also demonstrated by the following Examples X–XII.

EXAMPLES

Unless otherwise noted, in the following examples reactions are run in flame-dried round-bottomed flasks under an atmosphere of ultra high purity (UHP) argon. Diethyl ether (ether) and tetrahydrofuran (THF) are distilled from sodium benzophenone ketyl prior to use. Methylene chloride ($CH_2Cl_2$) is distilled from calcium hydride prior to use. All other compounds are purchased from Aldrich Chemical Company and used without further purification. Analytical thin-layer chromatography (TLC) is conducted with Silica Gel 60 $F_{254}$ plates (250 μm thickness, Merck). Column chromatography is performed using short path silica gel (particle size <230 mesh), flash silica gel (particle size 400–230 mesh), or Florisil® (200 mesh). Yields are not optimized. Purity of products is judged to be >95% based on their chromatographic homogeneity. High performance liquid chromatography (HPLC) is carried out with a Rainin HPLX system equipped with two 25 mL/min preparative pump heads using Rainin Dynamax 10 mm×250 mm (semi-preparative) columns packed with 60 Å silica gel (8 μm pore size), either as bare silica or as C-18-bonded silica. Melting points are measured using a Mel-Temp metal-block apparatus and are uncorrected. Nuclear magnetic resonance (NMR) spectra are obtained either on a Varian XL-400 spectrometer, operating at 400 MHz for $^1$H and 100 MHz for $^{13}$C or on a Varian XL-500 spectrometer, operating at 500 MHz for $^1$H and 125 MHz for $^{13}$C. Chemical shifts are reported in parts per million (ppm, δ) downfield from tetramethylsilane. Infrared (IR) spectra are obtained using a Perkin-Elmer 1600 FT-IR spectrometer. Resonances are reported in wavenumbers ($cm^{-1}$). Low and high resolution mass spectra (LRMS and HRMS) are obtained with electronic or chemical ionization (EI or CI) either (1) at Johns Hopkins University on a VG Instruments 70-S spectrometer run at 70 eV for EI and run with ammonia ($NH_3$) as a carrier gas for CI, or (2) at the University of Illinois at Champaign-Urbana on a Finnigan-MAT CH5, a Finnigan-MAT 731, or a VG Instruments 70-VSE spectrometer run at 70 eV for EI and run with methane (CH4) for CI.

EXAMPLE I (1'S,3aR,4S,7aS)-1'-(1'-methyl-2-hydroxyethyl)-1-octahydro-7a-methyl-22-hydroxy-1H-inden-4-ol(+)-6

To a suspension of paraformaldehyde (272 mg, 9.1 mmol) in 50 mL of $CH_2Cl_2$ is added 13.5 mL (13.5 mmol) of 1 M dimethylaluminum chloride solution in hexanes at −78° C. After 30 min, a solution of (+)-5 (503 mg, 2.8 mmol) in 5 mL of $CH_2Cl_2$ is added into the mixture at −78° C., and then the reaction mixture is warmed up to −40° C. After being stirred for 16 h at −40° C., the reaction mixture is quenched with 10% $K_2HPO_4$ at −40° C., and then warmed up to room temperature. The reaction mixture is extracted with EtOAc (2×100 mL), washed with 10% HCl, saturated aqueous $NaHCO_3$ solution, brine, dried, concentrated in vacuo, and then purified by chromatography (50% EtOAc/hexanes) to give 400 mg (68%) of (+)-6 as a white solid. mp. 84–87° C.; $[\alpha]^{25}D+35.0$ (c 6.8, EtOH).

EXAMPLE II

C,D-Ring TES tosylate (+)-7

To a solution of the diol (+)-6 of Example I (210 mg, 1.0 mmol) and 4-dimethylaminopyridine (DMAP, 210 mg, 1.7 mmol) in 15 mL of $CH_2Cl_2$ is slowly added the solution of p-toluenesulfonyl chloride (210 mg, 1.1 mmol) in 5 mL of $CH_2Cl_2$ at 0° C. After being stirred for 12 h at 0° C., the reaction mixture is quenched with water and diluted with $CH_2Cl_2$. The organic phase is separated, and the aqueous phase is extracted with $CH_2Cl_2$. The organic portions are combined, washed with brine, dried, concentrated in vacuo, and then purified by chromatography (25% EtOAc/hexanes) to give 337 mg (93%) of the desired tosylate as a colorless oil: $[\alpha]^{25}D+27.0$ (c 16.7, $CHCl_3$).

To a solution of the tosylate (337 mg, 0.93 mmol) and 2,6-lutidine (0.34 mL, 2.9 mmol) in 20 mL of $CH_2Cl_2$ is added triethylsilyl trifluoromethanesulfonate (TESOTf, 0.25 mL, 1.1 mmol) dropwise at −78° C. After 30 min, the reaction is quenched with water, extracted with pentane, washed with 5% HCl (2×30 mL), brine, dried, and then concentrated in vacuo. Purification by chromatography (5% EtOAc/hexanes) gives 386 mg (86%) of compound (+)-7 as a colorless oil: $[\alpha]^{25}D+47.9$ (c 4.7, $CHCl_3$).

EXAMPLE III

TES aldehyde (+)-8

A mixture of the tosylate (+)-7 of Example II (386 mg, 0.81 mmol) and KCN (184 mg, 2.8 mmol) in 30 mL of anhydrous dimethylsulfoxide (DMSO) is stirred for 3 h at 65° C. After being cooled to room temperature, the reaction mixture is quenched with water, extracted with ether, washed with brine, dried, and then concentrated in vacuo. Purification by chromatography (10% ether/hexanes) gives 234 mg (87%) of the desired nitrile as a colorless oil: $[\alpha]^{25}D+43.8$ (c 8.4, CHCl$_3$).

To a solution of the nitrile (234 mg, 0.70 mmol) in 30 mL of anhydrous toluene is added dropwise 1.4 mL (1 M solution in toluene, 1.4 mmol) of diisobutylaluminum hydride (DIBAH) at 0° C. After being stirred for an additional 20 min at 0° C., the mixture is diluted with ether, quenched with 5% HCl, extracted with ether, washed with brine, dried, and then concentrated in vacuo. Purification by chromatography (5% ether/hexanes) gave 200 mg (85%) of compound (+)-8 as a colorless oil: $[\alpha]^{25}D+38.8$ (c 7.1, CHCl$_3$).

EXAMPLE IV
Difluoro C,D-ring ethyl ester 9

A suspension of activated zinc powder (195 mg, 3.0 mmol) and ethyl bromodifluoroacetate (0.39 mL, 3.0 mmol) in 6 mL of THF is refluxed for 20 min and then cooled to 0° C. To this was added the solution of the aldehyde (+)-8 of Example III (200 mg, 0.59 mmol) in 5 mL of THF. The reaction mixture is warmed up to room temperature followed by refluxing for 20 min, and is then cooled to room temperature. The reaction mixture is poured into 1 M KHSO$_4$ and extracted with EtOAc (2×30 mL). The combined extracts are successively washed with 1 M KHSO$_4$ and brine, dried, and then concentrated. The resulting mixture is purified by column chromatography (10% ether/hexanes) to give 162 mg (59%) of a 1:1 mixture of diastereomers of the desired alcohol 9 as a colorless oil.

EXAMPLE V
Difluoro ethyl ester (+)-10

To a solution of ethyl ester 9 of Example IV (162 mg, 0.34 mmol) and pyridine (0.12 mL, 1.5 mmol) in CH$_2$Cl$_2$ (5 mL) is added phenyl chlorothianocarbonate (0.1 mL, 0.72 mmol). After being stirred at room temperature for 20 h, the reaction mixture is quenched with water, and then extracted with ether. The organic portions are combined and washed with saturated NaHCO$_3$ solution, brine, dried, concentrated in vacuo, and then purified by chromatography (5% ether/hexanes) to give 186 mg (90%) of the desired phenylthianocarbonate as diastereomeric mixtures.

To the solution of the resulting phenylthianocarbonate (186 mg, 0.31 mmol) in anhydrous benzene (10 mL) are added 2,2'-azobiisobutyronitrile (AIBN, 10 mg) and Bu$_3$SnH (0.13 mL, 0.48 mmol) at room temperature. After being refluxed for 3 h, the mixture is cooled to 0° C., quenched with water, and extracted with EtOAc. The combined organic portions are washed with brine, dried, and then purified by column chromatography (5% ether/hexanes) to give 125 mg (90%) of the desired deoxygenated difluoro ester 10 as a colorless oil: $[\alpha]^{25}D+16.9$ (c 1.5, CHCl$_3$).

EXAMPLE VI
16-Ene-24-Difluoro Alcohols (+)-11 and (+)-12

A. Using MeLi: A solution of ester 10 of Example V (65 mg, 0.15 mmol) in THF (3 mL) is treated with 1.4 M solution of MeLi (0.42 mL, 0.60 mmol) in ether at −78° C., and then is warmed up to room temperature. The mixture is cooled to 0° C., diluted with ether, and then quenched with saturated NH$_4$Cl solution. The mixture is extracted with EtOAc, washed with brine, dried, concentrated in vacuo, and then purified by column chromatography (10% EtOAc/hexanes) to give 52 mg (83%) of (+)-11 as a colorless oil: $[\alpha]^{25}D+23.8$ (c 6.5, CHCl$_3$).

B. Using EtLi: A solution of difluorinated C,D-ring ester 10 of Example V (68 mg, 0.15 mmol) and 5.0 mL of THF is cooled to −78° C., and then 0.5 mL (0.75 mmol, 1.5 M solution in THF) of EtLi is added dropwise to the solution. The reaction mixture is warmed up to room temperature, and then quenched with 10% HCl at −78° C., and extracted with EtOAc, washed with brine, dried, concentrated in vacuo, and then purified by column chromatography (10% EtOAc/hexanes) to give 66 mg (94%) of C,D-ring alcohol (+)-12 as a colorless oil: $[\alpha]^{25}D+18.2$ (c 3.7, CHCl$_3$).

EXAMPLE VII
24-Difluoro C,D-Ring Ketones (+)-13 and (+)-14

A. Ketone (+)-13: A solution of silyl ether 11 of Example VI (65 mg, 0.15 mmol) in THF (3 mL) and 0.45 mL of 1 M solution of tetra-n-butylammonium fluoride (TBAF) in THF is stirred for 16 h at room temperature. The mixture is quenched with water and extracted with EtOAc. The combined organic portions are washed with brine, dried, concentrated in vacuo, and then purified by chromatography (30% EtOAc/hexanes) to give 47 mg (99%) of the desired alcohol as a colorless oil: $[\alpha]^{25}D+8.5$ (c 4.7, CHCl$_3$); $^1$H NMR (400 MHz, CDCl$_3$) δ 5.32 (br d, J=1.6 Hz, 1 H), 4.17 (br s, 1H), 2.02–2.10 (m, 1H), 1.70–2.00 (m, 9H), 1.50–1.69 (m, 3H), 1.40 (td, J=13.2, 3.6 Hz, 1H), 1.27 (s, 6H), 1.02 (s, 3H), 1.01 (d, J=6.8 Hz, 3 H); $^{13}$C NMR (100 MHz, CDCl$_3$) δ 159.18, 125.38 (J=246 Hz), 120.10, 77.20 (J=27 Hz), 69.10, 54.34, 46.25, 35.37, 33.80, 31.52, 30.21, 28.96 (J=24 Hz), 27.38 (J=3.0 Hz), 23.52, 22.37, 18.25, 17.77; IR (neat, cm$^{-1}$) 3396, 2931, 1454, 1381; MS m/z (70 eV, EI) 316 (M$^+$); HRMS m/z (M$^+$) calcd 316.2214 for C$_{18}$H$_{30}$F$_2$O$_2$, found 316.2216.

To a solution of this diol (47 mg, 0.15 mmol) in CH$_2$Cl$_2$ (5 mL) are added 160 mg of oven-dried Celite and pyridinium dichromate (PDC., 163 mg, 0.43 mmol) at room temperature. After stirring at room temperature for 3.5 h, the mixture is passed through a 2 cm pad of flash silica gel, and then washed with EtOAc. The filtrate is concentrated and chromatographed with 30% EtOAc in hexanes to give 39 mg (84%) of ketone as a colorless oil: $[\alpha]^{25}D+20.6$ (c 3.9, CHCl$_3$); $^1$H NMR (400 MHz, CDCl$_3$) δ 5.30 (t, J=1.6 Hz, 1H), 2.84 (dd, J=10.8, 6.4 Hz, 1H), 2.43 (ddt, J=16.0, 10.8, 1.6 Hz, 1H), 2.30–2.56 (m, 2H), 2.04–2.17 (m, 3H), 1.72–2.02 (m, 6H), 1.59–1.69 (m, 1H), 1.27 (s, 6H), 1.07 (d, J=6.8 Hz, 3H), 0.79 (s, 3H); $^{13}$C NMR (100 MHz, CDCl$_3$) δ 210.97, 157.07, 125.27 (J=246 Hz), 120.72, 73.16 (J=27 Hz), 63.07, 53.73, 40.46, 34.30, 32.50, 28.65 (J=24 Hz), 27.30 (J=3.0 Hz), 27.07, 23.99, 23.50, 21.62, 17.18; IR (neat, cm$^{-1}$) 3448, 2942, 1711, 1456, 1380; MS m/z (70 eV, EI) 314 (M$^+$); HRMS m/z (M$^+$) calcd 314.2057 for C$_{18}$H$_{28}$F$_2$O$_2$, found 314.2053.

To a solution of this keto alcohol (39 mg, 0.12 mmol) in CH$_2$Cl$_2$ (3 mL) is added trimethylsilyl imidazole (TMS-imidazole, 35 μL, 0.24 mmol) at room temperature. After being stirred for 16 h at room temperature, the mixture is concentrated in vacuo and then chromatographed with 10% EtOAc in hexanes to give 47 mg (97%) of (+)-13 as a colorless oil: $[\alpha]^{25}D+18.1$ (c 4.7, CHCl$_3$); $^1$H NMR (400 MHz, CDCl$_3$) δ 5.31 (t, J=1.6 Hz, 1H), 2.84 (dd, J=10.8, 6.4 Hz, 1H), 2.44 (ddt, J=16.0, 10.8, 1.6 Hz, 1H), 2.26–2.31 (m, 2H), 2.05–2.15 (m, 3H), 1.68–2.05 (m, 6H), 1.59–1.66 (m, 1H), 1.26 (s, 6H), 1.07 (d, J=6.8 Hz, 3H), 0.80 (s, 3H), 0.10 (s, 9H); $^{13}$C NMR (100 MHz, CDCl$_3$) δ 210.89, 157.11, 125.02 (J=246 Hz), 120.61, 75.82 (J=27 Hz), 63.10, 53.74, 40.51, 34.32, 32.59, 28.42 (J=24 Hz), 27.37 (J=3.0 Hz), 27.07, 24.42 (J=2.6 Hz), 24.27 (J=3.0 Hz), 24.02, 21.89, 17.09, 2.30; IR (neat, cm$^{-1}$) 2958, 2873, 1721, 1458, 1383; MS m/z (70 eV, EI) 386 (M$^+$); HRMS m/z(M$^+$) calcd 386.2453 for C$_{21}$H$_{36}$F$_2$O$_2$Si, found 386.2457.

B. Ketone (+)-14: Difluorinated C,D-ring silyl ether 12 of Example VI (105 mg, 0.23 mmol) is dissolved in 3 mL of THF. To this solution is added dropwise 1 mL (1.0 M solution in THF, 1.0 mmol) of TBAF. The reaction mixture is stirred overnight at room temperature, then it is quenched with water and extracted with EtOAc. The combined organic portions are washed with brine, dried, concentrated in vacuo, purified by column chromatography (20% EtOAc/hexanes) to give 78 mg (99%) of the deprotected alcohol as a colorless oil: $[\alpha]^{25}D+8.7$ (c 5.4, $CHCl_3$); $^1H$ NMR (400 MHz, $CDCl_3$) δ 5.32 (t, J=1.6 Hz, 1H), 4.16 (d, J=2.4 Hz, 1H), 2.21–2.30 (m, 1H), 2.01–2.06 (m, 1H), 1.93–2.00 (m, 1H), 1.50–1.90 (m, 13H), 1.33–1.43 (m, 2H), 1.02 (s, 3H) 1.00 (d, J=7.2 Hz, 3H), 0.86–0.93 (tt, J=7.6 Hz, 1.2 Hz, 6H); $^{13}C$ NMR (100 MHz, $CDCl_3$) δ 159.47, 126.59 (t, J=247.8 Hz), 120.47, 77.04, 69.39, 54.60, 46.50, 35.61, 34.10, 31.78, 30.44, 29.87 (t, J=25.3 Hz), 27.52, 25.58, 25.47, 22.65, 18.49, 18.00, 7.81; IR (neat, $cm^{-1}$) 3604, 3430, 1460; MS m/z(70 eV, EI) 344 ($M^+$); HRMS m/z ($M^+$) calcd 344.2527 for $C_{20}H_{34}F_2O_2$, found 344.2533.

To the solution of the deprotected C,D-ring alcohol (67 mg, 0.20 mmol) in 3.0 mL $CH_2Cl_2$ are added 3 Å molecular sieves (0.6 g) and pyridinium chlorochromate (PCC., 320 mg, 1.50 mmol). The mixture turns dark red, and is stirred overnight. The reaction mixture is then passed through a short silica gel pad, washed with ether, concentrated, and then purified by column chromatography (20% EtOAc/hexanes) to give 52 mg (79%) of the desired C,D-ring keto alcohol as a colorless oil: $[\alpha]^{25}D+19.8$ (c 4.3, $CHCl_3$); $^1H$ NMR (400 MHz, $CDCl_3$) δ 5.31 (t, J=1.2 Hz, 1H), 2.85 (dd, J=6.4 Hz, 10.4 Hz, 1H), 2.45 (ddt, J=16.0, 10.8, 1.6 Hz, 1H), 2.25–2.31 (m, 2H), 1.54–2.20 (m, 14H), 1.08 (d, J=6.8 Hz, 3H), 0.90 (t, J=7.6 Hz, 6H), 0.80 (s, 3H); $^{13}C$ NMR (100 MHz, $CDCl_3$) δ 210.90, 157.06, 126.25 (t, J=247.4 Hz), 120.75, 76.75 (t, J=23.6 Hz), 63.10, 53.75, 40.49, 34.33, 32.54, 29.34 (t, J=24.4 Hz), 27.23 (t, J=3.8 Hz), 27.09, 25.28 (t, J=1.9 Hz), 24.02, 21.17, 17.21, 7.57; IR (neat, $cm^{-1}$) 3448, 2955, 1713, 1455; MS m/z(70 eV, EI) 342 ($M^+$); HRMS m/z ($M^+$) calcd 342.2370 for $C_{20}H_{32}F_2O_2$, found 342.2368.

To a solution of this C,D-ring keto alcohol (47.4 mg, 0.14 mmol) and 4.0 mL of $CH_2Cl_2$ is added 41 μL (0.28 mmol) of TMS-imidazole at room temperature. After being stirred for 16 h at room temperature, the reaction mixture is concentrated and purified by column chromatography (17% EtOAc/hexanes) to give 54 mg (94%) of the protected C,D-ring ketone (+)-14 as a colorless oil: $[\alpha]^{25}D+15.4$ (c 4.9, $CHCl_3$); $^1H$ NMR (400 MHz, $CDCl_3$) δ 5.29 (t, J=1.6 Hz, 1H), 2.84 (dd, J=6.4 Hz, 10.4 Hz, 1H), 2.44 (ddt, J=16.0, 10.8, 1.6 Hz, 1H), 2.20–2.32 (m, 2H), 1.48–2.34 (m, 14H), 1.06 (d, J =6.8 Hz, 3H), 0.84 (t, J=7.6 Hz, 6H), 0.78 (s, 3H), 0.08 (s, 9H); $^{13}C$ NMR (100 MHz, $CDCl_3$) δ 210.91, 157.05, 126.40 (t, J=247.4 Hz), 120.65, 80.65 (t, J=25.4 Hz), 63.11, 53,76, 40.53, 34.34, 32.59, 29.57 (t, J=24.4 Hz), 27.23 (t, J=3.8 Hz), 27.08, 26.08, 25.93, 24.04, 21.93, 17.14, 8.17, 8.09, 2.40; IR (neat, $cm^{-1}$) 2958, 1721; MS m/z(70 eV, EI) 414; HRMS m/z ($M^+$) calcd 414.2766 for $C_{23}H_{40}F_2O_2Si$, found 414.2775.

EXAMPLE VIII

Synthesis of 16-Ene-24-difluoro Calcitriol Analogs (−)-3a and (+)-3b

A solution of 96 mg (0.16 mmol) of phosphine oxide (±)-15 in 1.5 mL of anhydrous THF is treated dropwise with 100 μL (0.15 mmol) of 1.5 M solution of phenyllithium in THF under argon at −78° C. The resulting reddish orange solution is stirred for 30 min at −78 ° C. To the solution is added dropwise a solution of 43 mg (0.11 mmol) of C,D-ring ketone (+)-13 of Example VII in 1 mL of anhydrous THF. The reaction mixture is stirred until reddish orange color turns to pale yellow, and then is quenched with 3 mL of a 1:1 mixture of 2 N sodium potassium tartrate and 2 N $K_2CO_3$ solution, extracted with EtOAc (50 mLx2) and washed with brine. The combined organic portions are dried, concentrated in vacuo, and then purified by chromatography (3% EtOAc/hexanes) to afford 55 mg (66%) of the coupled product as a colorless oil. The silyl ethers are dissolved in 3 mL of anhydrous THF. To the solution are added 0.44 mL (0.44 mmol) of 1 M TBAF solution in THF, and 43 μL (0.31 mmol) of triethylamine. After 16 h at room temperature, the mixture is quenched with water, extracted with EtOAc (2×50 mL) and washed with brine. The combined organic portions are dried, concentrated in vacuo, and then purified by chromatography (EtOAc/hexanes/$NEt_3$=90/10/1) to afford 33 mg (98%) of a mixture of two diastereomers as a white solid. The diastereomers are separated by reverse phase HPLC. (C-18 semipreparative column, 60% MeCN/$H_2O$, 3 ml/min) to afford 12.5 mg (24%) of (−)-3a (1α, 3β, $t_R$ 24.4 min) as a foaming solid and 13.6 mg (27%) of (+)-3b (1β, 3α, $t_R$ 29.9 min) as a viscous oil. (−)-3a (1α, 3β): $[\alpha]^{25}D$ -14.0 (c 0.4, EtOH); $^1H$ NMR (400 MHz, $CDCl_3$) δ 6.32 (d, J=11.2 Hz,1H), 6.04 (d, J=11.2 Hz,1H), 5.32 (t, J=1.2 Hz, 1H), 5.18 (d, J=1.6 Hz, 1H), 5.03 (d, J=2.0 Hz, 1H), 3.93–4.00 (m, 1H), 3.52–3.59 (m, 2H), 2.78–2.83 (m,1H), 2.59–2.67 (m, 2H), 2.37 (dd, J=9.6, 6.4 Hz, 1H), 2.12–2.30 (m, 3H), 1.97–2.02 (m, 2H), 1.50–1.90 (m, 10H), 1.29 (s, 6H), 1.06 (d, J=6.8 Hz, 3H), 0.68 (s, 3H); $^{13}C$ NMR (100 MHz, $CD_3OD$) δ 160.44, 147.54, 141.95, 136.22, 126.67 (t, J=245 Hz), 123.92, 121.89, 118.88, 114.14, 73.62 (t, J=27 Hz), 67.39, 64.68, 59.77, 51.13, 47.38, 46.55, 37.64, 36.52, 33.89, 30.41, 29.93 (t, J=25 Hz), 29.74, 28.65(t, J=3 Hz), 24.73, 23.88 (t, J=21 Hz), 22.27, 17.25; W (MeOH) λmax 262 nm (ε21,400); IR (neat, $cm^{-1}$) 3350, 2930, 1378, 1043; MS m/z (70 eV, CI) 482 ($M+NH_4^+$); HRMS m/z ($M^+$) calcd 464.3102 for $C_{28}H_{42}F_2O_3$, found 464.3102. (+)-3b (1β,3α): $[\alpha]^{25}D+93.0$ (c 0.5, EtOH); $^1H$ NMR (400 MHz, $CDCl_3$) δ 6.31 (d, J=11.2 Hz, 1H), 6.04 (d, J=11.2 Hz, 1H), 5.28 (t, J=1.2 Hz, 1H), 5.16 (dd, J=2.0, 0.8 Hz, 1H), 5.00 (d, J=2.0 Hz, 1H), 4.00 (septet, J=4.0 Hz, 1H), 3.57–3.65 (m, 2H), 2.79–2.83 (m, 1H), 2.58–2.67 (m, 2H), 2.37 (dd, J=11.2, 6.4 Hz, 1H), 2.29 (dd, J=12.4, 6.4 Hz, 1H), 2.13–2.23 (m, 2H), 2.00 (dddd, J=14.8, 9.6, 6.4, 3.2 Hz, 1H), 1.50–1.88 (m, 11H), 1.28 (s, 6H), 1.06 (d, J=6.8 Hz, 3H), 0.66 (s, 3H); $^{13}C$ NMR (100 MHz, $CDCl_3$) δ 158.90, 145.30, 142.41, 134.30, 125.38 (t, J=245 Hz), 123.58, 120.72, 116.83, 113.77, 73.29 (t, J=27 Hz), 67.12, 64.34, 58.31, 59.96, 46.19, 44.32, 37.38, 35.23, 32.56, 29.33, 28.77, 28.74 (t, J=25 Hz), 27.28 (t, J=3 Hz), 23.58 (2C), 21.71, 16.72; UV (MeOH) λmax 262 nm (ε16,100); IR (neat, $cm^{-1}$) 3366, 2930, 2874, 1369, 1178, 1040; MS m/z (70 eV, CI) 482 ($M+NH_4^+$), 446 ($M+NH_4^+$); HRMS m/z ($M^+$) calcd 464.3102 for $C_{28}H_{42}F_2O_3$, found 464.3107.

EXAMPLE IX

Synthesis of 16-Ene-24-difluoro Calcitriol Analogs (−)-4a and (+)-4b

A solution of 69.4 mg (0.12 mmol) of phosphine oxide (±)-15 in 2.0 mL of anhydrous THF is cooled to −78° C. and treated with 81 μL (0.12 mmol, 1.5 M solution in THF) of phenyllithium under argon atmosphere. The mixture turns reddish orange and is stirred for 30 min at −78° C. To the solution is added dropwise a solution of 47.9 mg (0.12 mmol) of the C,D-ring ketone (+)-14 of Example VII in 1.0 mL of anhydrous THF. The reaction keeps going on until the reddish orange color fades to yellow (about 6 hours). The reaction is quenched by adding 3.0 mL of a 1:1 mixture of 2 N sodium potassium tartrate and 2 N $K_2CO_3$ solution. The reaction mixture is extracted with EtOAc, washed with brine, dried, concentrated in vacuo, and then purified by column chromatography (97% hexanes/ether) to afford 68.0 mg (74%) of the coupled product as a colorless oil. The silyl ethers are dissolved in 3.0 mL of anhydrous THF, and to this solution is added TBAF (0.52 mL, 0.52 mmol, 1.0 M solution in THF) and 52 µL (0.39 mmol) of $Et_3N$. The reaction is run in darkness overnight, then quenched with water and extracted with EtOAc. The combined organic portions are washed with brine, dried, concentrated in vacuo and then purified by column chromatography (90% EtOAc/hexanes) to give 38.7 mg (92%) of a mixture of two diastereomers as a white solid. The diastereomers are separated by reverse phase HPLC (C-18 semipreparative column, 60% $MeCN/H_2O$, 3.0 mL/min) to afford 14.0 mg (24%) of (−)-4a (1α,3β, $t_R$ 48.5 min) as a colorless oil and 15.5 mg (26%) of (+)-4b (1β,3α, $t_R$ 57.3 min) as a foaming solid. (−)-4a: $[\alpha]^{25}D$−1.3 (c 1.4, EtOH); $^1H$ NMR (400 MHz, $CDCl_3$) δ 6.32 (d, J=11.2 Hz, 1H), 6.04 (d, J=11.2 Hz, 1H), 5.32 (t, J=1.6 Hz, 1H), 5.18 (d, J=1.6 Hz, 1H), 5.03 (d, J=2.0 Hz, 1H), 3.97 (septet, J=4.0 Hz, 1H), 3.50–3.60 (m, 2H), 2.77–2.85 (m, 1H), 2.57–2.69 (m, 2H), 2.10–2.40 (m, 4H), 1.44–2.02 (m, 16H), 1.06 (d, J=6.8 Hz, 3H), 0.91 (t, J=7.6 Hz, 6H), 0.68 (s, 3H); $^{13}C$ NMR (100 MHz, $CD_3OD$) δ 160.37, 147.52, 141.91, 136.61, 127.57 (t, J=247.3 Hz), 123.88, 121.91, 118.88, 114.12, 77.56 (t, J=24.7 Hz), 67.37, 64.67, 59.76, 51.12, 47.38, 46.52, 37.64, 36.51, 33.92, 30.60 (t, J=24.2 Hz), 30.40, 29.73, 28.53, 25.87 (d, J=6.8 Hz), 24.73, 22.32, 17.26, 7.99; IR (neat, $cm^{-1}$) 3350, 2919, 1607, 1449; UV (EtOH) λmax 263 nm (ϵ17,500); MS m/z (70 eV, EI) 492 ($M^+$); HRMS m/z ($M^+$) calcd 492.3415 for $C_{30}H_{46}F_2O_3$, found 492.3412. (+)-4b: $[\alpha]^{25}D$+78.0 (c 1.6, EtOH); $^1H$ NMR (400 MHz, $CDCl_3$) δ 6.31 (d, J=11.2 Hz, 1H), 6.04 (d, J=11.2 Hz, 1H), 5.32 (t, J=1.4 Hz, 1H), 5.15 (d, J=0.8 Hz, 1H), 5.00 (d, J=1.6 Hz, 1H), 4.02 (septet, J=4.0 Hz, 1H), 3.58–3.64 (m, 2H), 2.75–2.85 (m, 1H), 2.55–2.68 (m, 2H), 2.10–2.40 (m, 4H), 1.44–2.03 (m, 16H), 1.05 (d, J=6.8 Hz, 3H), 0.91 (t, J=7.6 Hz, 6H), 0.66 (s, 3H); $^{13}C$ NMR (100 MHz, $CD_3OD$) δ 160.43, 147.63, 142.06, 136.72, 127.57 (t, J=242.6 Hz), 123.83 (d, J=3.8 Hz), 121.89 (d, J=8.3 Hz), 118.83, 113.79, 77.56 (t, J=24.7 Hz), 67.43, 64.62, 59.71, 51.07, 47.36, 46.32, 37.60, 36.57, 33.90, 30.60 (t, J=24.2 Hz), 30.23, 29.74, 28.53 (t, J=3.8 Hz), 25.86 (d, J=6.8 Hz), 24.64, 22.33, 17.25, 7.99; IR (neat, $cm^{-1}$) 3342, 2931, 1648, 1625, 1455; UV (EtOH) λmax 262 nm (ϵ18,000); MS m/z (70 eV, EI) 492 ($M^+$); HRMS m/z ($M^+$) calcd 492.3415 for $C_{30}H_{46}F_2O_3$, found 492.3417.

EXAMPLE X

Antiproliferative assays using malignant melanoma cells

Figure 2:
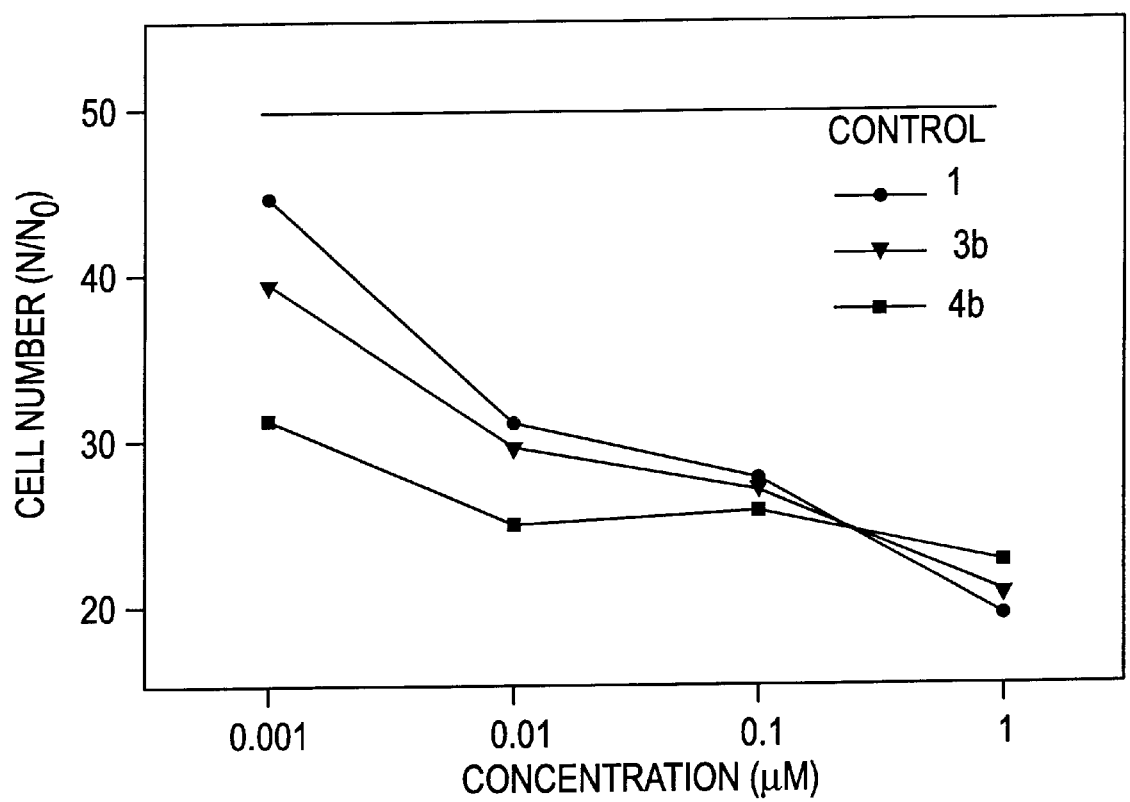

Each of these new hybrid analogs (Structures 3 and 4 of Scheme I) is evaluated initially for in vitro antiproliferative activity in murine keratinocytes, using the protocol described in Posner et al., *J. Med. Chem.* 1992, 35, pp. 3280–3287. The procedure utilized is described as follows:

Murine B16 malignant melanoma cells are grown and propagated in RPMI medium supplemented with 10% fetal bovine serum, L-glutamine, penicillin, and streptomycin and incubated at 37° C. in 5% $CO_2$. For proliferation studies, cells are washed with PBS, trypsinized, and suspended in 8 ml of supplemented RPMI medium. The cell density is then determined using a hemacytometer and cells are resuspended in RPMI at 10,000 cells/$cm^3$. One ml of cell suspension (10,000 cells) is added to each well of a Falcon 24 Well Flat Bottom Tissue Culture Plate (Becton-Dickinson, Lincoln Park, N.J.). Plates are incubated for 24 hours to allow for cell attachment. The medium is then removed and replaced with fresh RPMI medium containing either 0.4% solvent (isopropanol) or vitamin D analog at concentrations ranging from 1–1000 nM in triplicate. When control wells near confluence, cells are washed with PBS, trypsinized, and suspended in 10 ml of Isoton II Coulter Balanced Electrolyte Solution in FISHERbrand Dilu-Vial cuvettes. Cell number is then determined for each well as an average of two readings on a ZM Coulter Counter. Results are expressed as the average cell number for each vitamin D analog treatment group divided by the intital cell number ($N/N_0$). Results are shown in FIGS. 1 and 2 of the drawing. The average standard deviation of the $N/N_0$ cell number measurements was 0.21 in FIG. 1 and 2.1 in FIG. 2.

As seen in the past with 1-(hydroxymethyl)-3-hydroxy diastereomeric pairs of hybrid analogs differing only in relative stereochemistry at the 1- and 3-positions (i.e. 1α,3β vs. 1β,3α), only those diastereomers with the unnatural 1β,3α a stereochemistry (i.e. Structures 3b and 4b) show significant antiproliferative activities. As shown in FIG. 1, the antiproliferative activity of both fluoro analogs 3b and 4b is at least equal to that of $1,25D_3$ even at physiologically relevant 7 nM concentrations. In sharp contrast, diastereomeric analogs, Structures 3a and 4a, are much less potent.

Because of their high antiproliferative activity in keratinocytes, fluorinated hybrid analogs, Structures 3b and 4b, were evaluated in vitro in murine malignant melanoma cells also. As shown in FIG. 2, even at 1 nM concentration, both of these hybrid analogs are more potent antiproliferative agents than $1,25D_3$.

EXAMPLE XI

In different experiments from those summarized in Example X and FIGS. 1 and 2, the in vitro vitamin D receptor-mediated transcriptional activities of the two most antiproliferative analogs, Structures 3b and 4b, are tested in rat osteosarcoma ROS 17/2.8 cells. The procedure utilized is described as follows:

Transfections and transcriptional activity of the analogs.

Rat osteosarcoma ROS 17/2.8 cells are maintained in 50% Dulbecco's modified Eagle medium (DMEM) and 50% F12 nutrient mixture supplemented with 10% fetal bovine serum. Forty eight hours before transfections, the cells are plated in 35-mm dishes at a density of $10^5$/dish in DMEM and 10% fetal bovine serum. ROS 17/2.8 cells are transfected with 2 µg of plasmid containing the vitamin D responsive element from the human osteocalcin gene (GGTGACTCACCGGGTGAACGGGGGCATT) attached to the thymidine kinase promoter/growth hormone fusion gene. All transfections are performed by the Diethylaminoethyl dextran method (see Peleg et al., *Henry Ford Hosp. J.* 1984, 37, pp. 144–147), and the cells are then treated for 1 min with 10% dimethyl sulfoxide, washed twice in phosphate buffered saline and incubated in DMEM suppemented with 10% fetal bovine serum without or with graded concentrations of the analogs. Medium samples for measurements of reporter gene expression (growth hormone) are collected 2 days after transfection. Growth hormone is measured by a radioimmunoassay as described by the manufacturer (Nichols Institute, San Juan Capistrano, Calif.).

In such testing, the non-homologated fluoro hybrid analog Structure 3b is found to be slightly more transcriptionally potent ($ED_{50}=2\times10^{-10}$M) than calcitriol ($ED_{50}=3\times10^{-10}$ M), and 26,27-homologated analog Structure 4b is found to be the most potent ($ED_{50}=5\times10^{-11}$M). The high transcriptional activities of fluoro hybrid analogs, Structures 3b and 4b, are especially noteworthy because they do not have the natural 1α-hydroxyl substituent on the A-ring that has previously been considered to be essential for high biological activity.

EXAMPLE XII

Because of their high antiproliferative and transcriptional activities in vitro, fluorinated hybrid analogs, Structures 3b and 4b, are evaluated for hypercalcemic effects in vivo. The procedure utilized is described as follows:

Determination of urinary calcium levels.

Male F344 rats (150 g) are housed individually in glass metabolism cages and received food and water ad libitum. After several days acclimation, rats receive 1 microgram per kg body weight of test compound per os for seven consecutive days in 150 microliters of propylene glycol/0.05M $Na_2HPO_4$ (80:20). Urine samples, which are collected on ice, were centrifuged at 650×g for 10 min, adjusted to pH 6.0 as necessary, and assayed for calcium content spectrophotometrically at 575 nm using reagents and standards from Sigma Calcium Kit #587.

Figure 3:
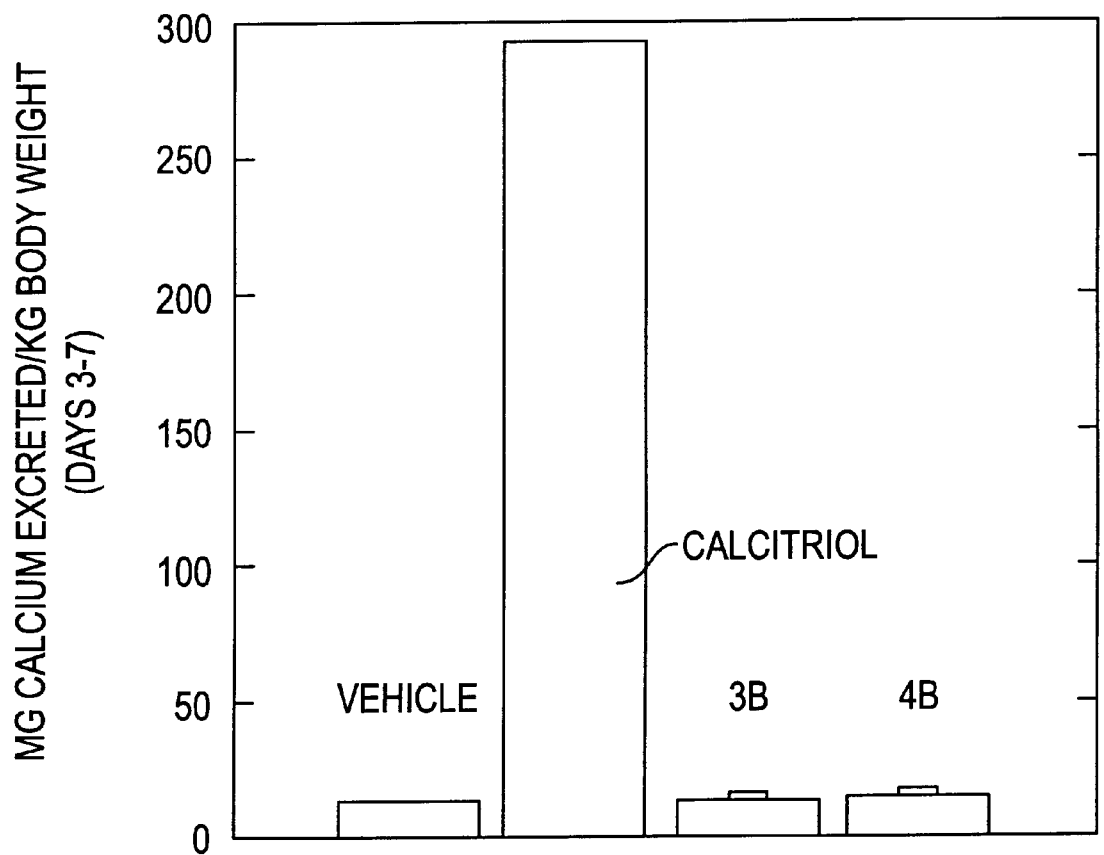

In contrast to $1,25D_3$, which produces marked excretion of calcium into the urine of rats treated daily for one week, the two fluorinated hybrid analogs, Structures 3b and 4b, produce no calcium elevation above control under identical treatment regimens. This is shown in FIG. 3 of the drawings. In addition, suppression of body weight gain seen with $1,25D_3$ is not observed with these hybrid analogs.

From the forgoing synthesis Examples I–IX, it can be seen that effective chemical syntheses of the four new 1-hydroxylmethyl-16-ene-24-fluorinated hybrid analogs of $1,25D_3$ have been achieved. From the forgoing performance Examples X–XII, it is apparent that of these new hybrid analogs, with their structural modification on both the A-ring and on the C,D-ring side-chain, difluoro hybrid analogs Structures 3b and 4b stand out as potential drug candidates based on their high antiproliferative and transcriptional potencies and based also on their apparent non-toxicity (non-calcemic activity) when administered orally to rats.

While the invention is described herein with reference to certain specific embodiments, it is not intended that the invention be limited thereto. It will be appreciated by persons of skill in the art that many variations are possible within the spirit and scope of the invention that can be achieved with no more than routine experimentation. References and patents cited herein are hereby incorporated by reference.

What is claimed is:

1. A fluorinated analog of 1α,25-dihydroxy vitamin $D_3$, having the structural formula:

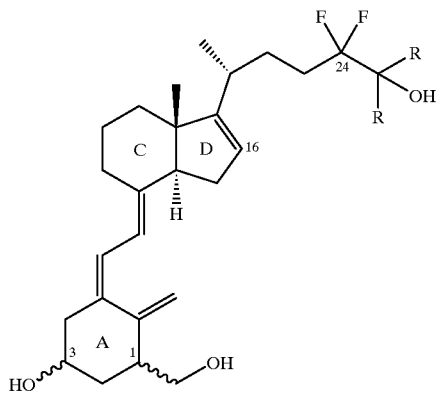

wherein the hydroxymethyl substituent at Position 1 of the A-ring and the hydroxy substituent at Position 3 of the A ring are such that said analogs have either the (−)(1α, 3β) or (+)(1β, 3α) diastereoisomeric configuration and wherein R is a $C_{1-4}$ straight-chained or branched alkyl or a $C_{1-7}$ cycloalkyl group.

2. The Vitamin $D_3$ analog according to claim 1 wherein R is a $C_{1-4}$ straight-chained or branched alkyl group.

3. The Vitamin D3 analog according to claim 2 which is a straight-chained alkyl group.

4. The Vitamin $D_3$ analog according to claim 2 which is in the (+)(1β, 3α) diastereoisomeric configuration.

5. A Vitamin $D_3$ analog according to claim 4 wherein R is methyl.

6. A Vitamin $D_3$ analog according to claim 4 wherein R is ethyl.

* * * * *